(12) United States Patent
Bonan et al.

(10) Patent No.: US 7,468,035 B2
(45) Date of Patent: Dec. 23, 2008

(54) AUTOMATED METHOD FOR DISCRIMINATING THE CARDIAC BEAT

(76) Inventors: Matteo Bonan, Via Bolognese 326, 50010 Florence (IT); Salvatore Romano, Via Arrigo Boito, 33 - 50144 Florence (IT)

(*) Notice: Subject to any disclaimer, the term of this patent is extended or adjusted under 35 U.S.C. 154(b) by 138 days.

(21) Appl. No.: 10/547,668

(22) PCT Filed: Mar. 11, 2004

(86) PCT No.: PCT/IT2004/000120

§ 371 (c)(1),
(2), (4) Date: Jul. 3, 2006

(87) PCT Pub. No.: WO2004/084088

PCT Pub. Date: Sep. 30, 2004

(65) Prior Publication Data

US 2006/0264766 A1    Nov. 23, 2006

(30) Foreign Application Priority Data

Mar. 17, 2003  (IT)  ............ RM2003A0117

(51) Int. Cl.
*A61B 5/02*  (2006.01)
(52) U.S. Cl. .................. 600/485; 600/500; 600/483

(58) Field of Classification Search ............. 600/481, 600/483, 484, 485, 500–503, 508, 509, 513
See application file for complete search history.

(56) References Cited

U.S. PATENT DOCUMENTS

| 6,592,528 | B2 * | 7/2003 | Amano ................ 600/485 |
| 6,616,613 | B1 * | 9/2003 | Goodman ............. 600/504 |
| 7,220,230 | B2 * | 5/2007 | Roteliuk et al. ...... 600/485 |
| 2002/0022785 | A1 | 2/2002 | Romano | |
| 2002/0072860 | A1 * | 6/2002 | Amano ................ 702/19 |
| 2003/0023173 | A1 | 1/2003 | Finkelstein et al. | |
| 2003/0036685 | A1 * | 2/2003 | Goodman ............. 600/300 |
| 2005/0124903 | A1 * | 6/2005 | Roteliuk et al. ...... 600/526 |

* cited by examiner

*Primary Examiner*—Charles A Marmor, II
*Assistant Examiner*—Navin Natnithithadha
(74) *Attorney, Agent, or Firm*—Young & Thompson

(57) ABSTRACT

An automated method for discriminating the cardiac beat, on the basis of a blood pressure sampled signal, having a starting point Pstart, operating according to a finite state machine for determining at least the diastolic point Pdia, the systolic point Psys, and the dicrotic point Pdic of the pressure signal, the method being apt to iteratively repeat on subsequent sections of the pressure signal; and instruments necessary to perform the automated method and the apparatus performing the same.

42 Claims, 4 Drawing Sheets

AUTOMATED METHOD FOR DISCRIMINATING THE CARDIAC BEAT

BACKGROUND OF THE INVENTION

The present invention concerns an automated method for discriminating the cardiac beat, starting from the analysis of a detected pressure curve, which is easily implementable, inexpensive and highly reliable, the method being apt to iteratively repeat itself for subsequent sections of the pressure signal.

The present invention further concerns the instruments necessary to perform the automated method and the apparatus performing the same.

DESCRIPTION OF THE RELATED ART

It is known that the evaluation of biological signals has a basic role in diagnostics and clinics.

In particular, several automated methods for evaluating the detected blood pressure curve have been developed in recent years, and they have been implemented in corresponding equipments.

However, such methods, and the related equipments, present some drawbacks.

First of all, they do not adapt to all the possible conditions of detection, which are variable depending on the patient, on the possible presence of pathologies, and on the measurement situation. By way of example, such equipments do not recognise the signal of an electrocardiogram obtained during a heart surgery operation.

Moreover, the more they are reliable, the more such equipments are complex and, consequently, expensive.

SUMMARY OF THE INVENTION

It is, therefore, an object of the present invention to provide an automated method for discriminating the cardiac beat, starting from the analysis of a detected pressure curve, which is easily implementable, inexpensive and highly reliable.

It is still an object of the present invention to provide the instruments necessary to perform the automated method and the apparatus performing the same.

It is specific subject matter of this invention an automated method for discriminating the cardiac beat, on the basis of a blood pressure sampled signal, having a starting point Pstart, characterised in that it operates according to a finite state machine, comprising:

A. a first state (1), wherein the method searches for:
   the pressure absolute minimum value Pmin, by scanning the pressure values included within a first time interval not exceeding the interval going from the starting point Pstart up to the point distant from the determined minimum value Pmin by a first time threshold DTMIN_SYS,
   the pressure absolute maximum value Pmax, by scanning the pressure values included within a second time interval not exceeding the interval going from the starting point Pstart up to the point distant from the determined minimum value Pmin by a second time threshold DTMAX_SYS, and
   the pressure signal first derivative maximum value Y1max_postdia included within a third time threshold not exceeding the interval going from the starting point Pstart up to the point distant from the determined minimum value Pmin by a period equal to the second time threshold DTMAX_SYS,
   the method assuming the point Pmin as diastolic point Pdia and the point Pmax as systolic point Psys, and passing to a following second state (2);

B. the second state (2), wherein the method searches for a pressure signal inflection point Pinflection following the systolic point Psys in a fifth time interval not exceeding the interval starting from the systolic point Psys and of duration equal to a third time threshold DTMAX_MINY1_SYS, the method then passing to a following third state (3);

C. the third state (3), wherein the method verifies whether, in a sixth time interval not exceeding the interval starting from the inflection point Pinflection and of duration equal to a fourth time threshold DTMAX_SYS2Y1DIC, the pressure signal presents a hump with downward concavity, so that:
   if the outcome of the verification is positive, the method searches, in a seventh time interval not exceeding the interval starting from the inflection point Pinflection and of duration equal to the fourth time threshold DTMAX_SYS2Y1DIC, for the first pressure curve relative minimum, and it assumes the latter as dicrotic point Pdic, whereas
   if the outcome of the verification is negative, the method searches in said seventh time interval the instant wherein the pressure signal second derivative assumes the maximum value Y2max_postinflection, and it assumes the related pressure signal point as dicrotic point Pdic,
   the method then passing to a following fourth state (4);

D. the fourth state (4), wherein the method searches for a maximum value Y1max_postdic of the pressure signal first derivative in an eighth interval not exceeding the interval starting from the dicrotic point Pdic and of duration equal to a fifth time threshold DPOSTDIC, the method verifying that the maximum value Y1max_postdia determined in the first state (1) is not less than the value Y1max_postdic, so that:
   if the outcome of the verification is negative, the method returns to the first state (1) assuming as new starting point Pstart a point following the diastolic point Pdia and not following the dicrotic point Pdic, whereas
   if the outcome of the verification is positive, the method passes to a final state (7); and E. the final state (7), wherein the method is apt to give the diastolic point Pdia, the systolic point Psys, and the dicrotic point Pdic.

Furthermore according to the invention, in the first state the method may also search for:
   the pressure signal second derivative maximum value Y2max_diatosys included within a fourth time interval not exceeding the interval going from the starting point Pstart up to the point distant from the determined minimum value Pmin by a period equal to the second time threshold DTMAX_SYS, so that in the fourth state the method may also search for a pressure signal second derivative maximum value Y2max_postdic within the eighth interval, the method also verifying that the maximum value Y2max_diatosys determined in the first state (1) is not less than the value Y2max_postdic, so that:
   if the outcome of the verification is negative, the method returns to the first state (1) assuming as new starting point Pstart a point following the diastolic point Pdia and not following the dicrotic point Pdic, whereas
   if the outcome of the verification is positive, the method passes to the final state (7).

Always according to the invention, in the first state (1), the assumption of the points Pmin and Pmax as diastolic Pdia and systolic Psys points, respectively, may depend on the outcome of the verification that the point Pmin precedes the point Pmax, so that:

if the outcome of the verification is negative, the method returns to perform all the operations of the first state assuming as new starting point Pstart a point not preceding Pmin, whereas if the outcome of the verification is positive, the point Pmin is assumed as diastolic point Pdia and the point Pmax is assumed as systolic point Psys and the method passes to the following second state.

Still according to the invention, the finite state machine according to which it operates may comprise a fifth state, the method passing from the fourth state to the final state by preliminarily passing to the fifth state, wherein the method determines a pressure signal point P3 corresponding to the instant t3 wherein the pressure signal second derivative assumes the absolute minimum value Y2 min_systodic within a ninth interval not exceeding the interval going from the systolic point Psys up to the dicrotic point Pdic, the method then passing to the final state wherein it is apt to give the point P3.

Preferably according to the invention, said ninth interval goes from the instant which is intermediate within the interval included between the systolic point Psys and the dicrotic point Pdic $$tsys+(tdic-tsys)/2$$

up to the instant of the dicrotic point Pdic $$tdic,$$

where tsys is the instant corresponding to the systolic point Psys and tdic is the instant corresponding to the dicrotic point Pdic.

Furthermore according to the invention, in the fourth state the method may verify whether the pressure signal has been detected in an aorta, so that:

if the outcome of the verification is positive, the method passes to the final state, whereas if the outcome of the verification is negative, the method passes to the fifth state.

In particular, such verification may occur on the basis of a datum concerning the signal detection site given as input by an operator. Advantageously, such input datum may set the value of a suitable register or flag of which the method may just verify the value in the fourth state.

Always according to the invention, the finite state machine according to which it operates may comprise a sixth state, at which the method arrives in the case when in the third state it has verified that the pressure signal presents a hump with downward concavity within the sixth time interval, the method arriving at the sixth state after the fourth state before passing to the final state, in the sixth state the method searching in said sixth time interval for the relative maximum point P4 after the dicrotic point Pdic, i.e. the hump apex, the method then passing to the final state wherein it is apt to give the point P4.

Still according to the invention, in the sixth state the method may also search for a pressure signal relative minimum point Pend within a tenth interval not exceeding the interval going from the dicrotic point Pdic up to the point Ptermination distant from the dicrotic point Pdic by a sixth time threshold DENDPOSTDIC, the method being apt to give in the final state the point Pend in the case when this has been determined in the sixth state.

Preferably according to the invention, the method searches for the point Pend after having determined the point P4 and said tenth interval goes from the point P4 up to the point Ptermination.

Always preferably according to the invention, the sixth time threshold DENDPOSTDIC is not longer than 150 milliseconds.

Furthermore according to the invention, the method may arrive at the sixth state starting from the fifth state.

Always according to the invention, in the first state the method may search for the first point Pdec following the starting point Pstart belonging to a pressure signal decreasing phase, the first time interval may go from the first decreasing point Pdec up to the point distant from the determined minimum value Pmin by a first time threshold DTMIN_SYS, and the second time interval may go from the first decreasing point Pdec up to the point distant from the determined minimum value Pmin by a second time threshold DTMAX_SYS.

Still according to the invention, the third and the four time intervals may go from the first decreasing point Pdec up to the point distant from the determined minimum value Pmin by a second time threshold DTMAX_SYS.

Furthermore according to the invention, the third and the four time intervals may go from the determined minimum value Pmin up to the point distant from the determined minimum value Pmin by a second time threshold DTMAX_SYS.

Alternatively according to the invention, the third and the four time intervals may go from the determined minimum value Pmin up to the determined maximum value Pmax.

Always according to the invention, in the second state the method may search for the point Pinflection by searching for the pressure signal first derivative absolute minimum value Y1min_postsys within the fifth time interval, assuming the pressure signal point wherein the first derivative thereof assumes the absolute minimum value Y1 min_postsys as inflection point Pinflection.

Still according to the invention, in the third state the method may verify whether in the sixth time interval the pressure signal presents a hump with downward concavity by searching for the pressure signal first derivative absolute maximum value Y1max_postsys and by verifying that this value Y1max_postsys is positive, whereby the pressure signal presents said hump in the case when the value Y1max_postsys is positive.

Furthermore according to the invention, in the third state the method may search within the seventh time interval for the pressure curve first relative minimum by searching for the instant wherein the pressure signal first derivative assumes the value of zero within said seventh time interval.

Always according to the invention, in the fourth state, the search for the first derivative maximum value Y1max_postdic and the second derivative maximum value Y2max_postdic of the pressure signal within the eighth interval, and the verification that both are not larger than the maximum values Y1max_postdia and Y2max_diatosys determined in the first state, may be carried out only in the case when in the third state the method has verified that the pressure signal presents a hump with downward concavity within the sixth time interval.

Still according to the invention, when the method returns from the fourth state to the first state, it may assume the point immediately preceding the determined dicrotic point Pdic as new starting point Pstart.

Preferably according to the invention, the first time threshold DTMIN_SYS is not longer than 200 milliseconds, still more preferably not longer than 150 milliseconds.

Always preferably according to the invention, the second time threshold DTMAX_SYS is not longer than 380 milliseconds, still more preferably not longer than 350 milliseconds.

Still preferably according to the invention, the third time threshold DTMAX_MINY1_SYS is not longer than 250 milliseconds, still more preferably not longer than 200 milliseconds.

Always preferably according to the invention, the fourth time threshold DTMAX_SYS2Y1DIC is not longer than 250 milliseconds, still more preferably not longer than 200 milliseconds.

Still preferably according to the invention, the fifth time threshold DPOSTDIC is not longer than 200 milliseconds, still more preferably not longer than 150 milliseconds.

Always preferably according to the invention, the pressure signal is sampled at a frequency of 1 kHz.

Furthermore according to the invention, from the final state the method may return to iteratively perform the first state by assuming a point following the dicrotic point Pdic as new starting point Pstart.

Always according to the invention, when the method arrives at the final state from the fourth or fifth state, from the final state the method may return to iteratively perform the first state by assuming a point following the dicrotic point Pdic and distant from this by a seventh time threshold DNEW as new starting point Pstart, preferably not shorter than 1 millisecond and not longer than 150 milliseconds.

Still according to the invention, when the method arrives at the final state from the sixth state, in the case when in the sixth state the point Pend has been determined, from the final state the method may return to iteratively perform the first state by assuming a point following the dicrotic point Pdic and preceding the point Pend as new starting point Pstart, preferably by assuming the point immediately preceding the point Pend as new starting point Pstart.

Furthermore according to the invention, when the method arrives at the final state from the sixth state, in the case when in the sixth state the point Pend has not been determined, from the final state the method may return to iteratively perform the first state by assuming a point following the dicrotic point Pdic and not following the point Ptermination as new starting point Pstart, preferably by assuming the point immediately preceding the point Ptermination as new starting point Pstart.

It is still specific subject matter of this invention a computer, comprising input and/or output interface means, memorizing means, and processing means, characterised in that it is apt to perform the previously described automated method for discriminating the cardiac beat.

It is further specific subject matter of this invention an apparatus for detecting and analyzing the blood pressure, comprising a computer and blood pressure detecting means, characterised in that said computer is the just illustrated computer.

It is another specific subject matter of this invention a computer program characterised in that it comprises code means adapted to execute, when running on a computer, the previously described automated method for discriminating the cardiac beat.

It is further specific subject matter of this invention a memory medium, readable by a computer, storing a program, characterised in that the program is the just described computer program.

BRIEF DESCRIPTION OF THE DRAWINGS

The present invention will be now described, by way of illustration and not by way of limitation, according to its preferred embodiments, by particularly referring to the Figures of the enclosed drawings, in which.

DESCRIPTION OF THE PREFERRED EMBODIMENT

In the Figures, same references are used to indicate alike elements.

The inventors have developed a method that allows the pressure signal to be recognised during a cardiac cycle, the objectivity of which is confirmed by the fact that the method is capable to recognise the signal obtained from an electrocardiogram carried out during a heart surgery operation. The method according to the invention examines the biological signals, searching for characteristic maximum and minimum points and characteristic intermediate points representing certain physiological states.

More specifically, the method according to the invention allows the pressure curve produced by the heart during its operation to be recognised. The inventors have developed the method taking into account the fact that the pressure wave of a cardiac beat assumes a series of well defined shapes, and they have determined the curve characteristic points, considering them as the events to be detected by the method. The method developed by the inventors operates as a finite state machine assuming different states in recognising the characteristic points of the cardiac beat.

In particular, for determining a cardiac beat in an arterial and/or venous system, the method according to the invention determines a systolic phase and a diastolic phase. The systolic phase culminates in reaching a pressure relative maximum, unless counterpulsations, whereas the diastolic phase culminates, unless pathological conditions, in reaching a pressure relative minimum. Moreover, the method further determines a third point, the dicrotic notch, which is associated with a cardiac beat. The dicrotic point is the point wherein the cardiac valve closes and it mathematically corresponds to a maximum point of the second derivative or to a relative minimum point of the pressure curve which occurs following the systolic point. Consequently, the finite state machine firstly determines these three points. Afterwards, in order to verify that the three determined points effectively correspond to a cardiac beat, the method according to the invention ascertains the presence of a series of subsequent events with a sequence equal to the just determined one. In the positive case that such sequence of subsequent events occurs, the method recognises the three previously determined points as characteristic ones of a cardiac beat ending at the diastolic point of the following beat.

Figure 1:
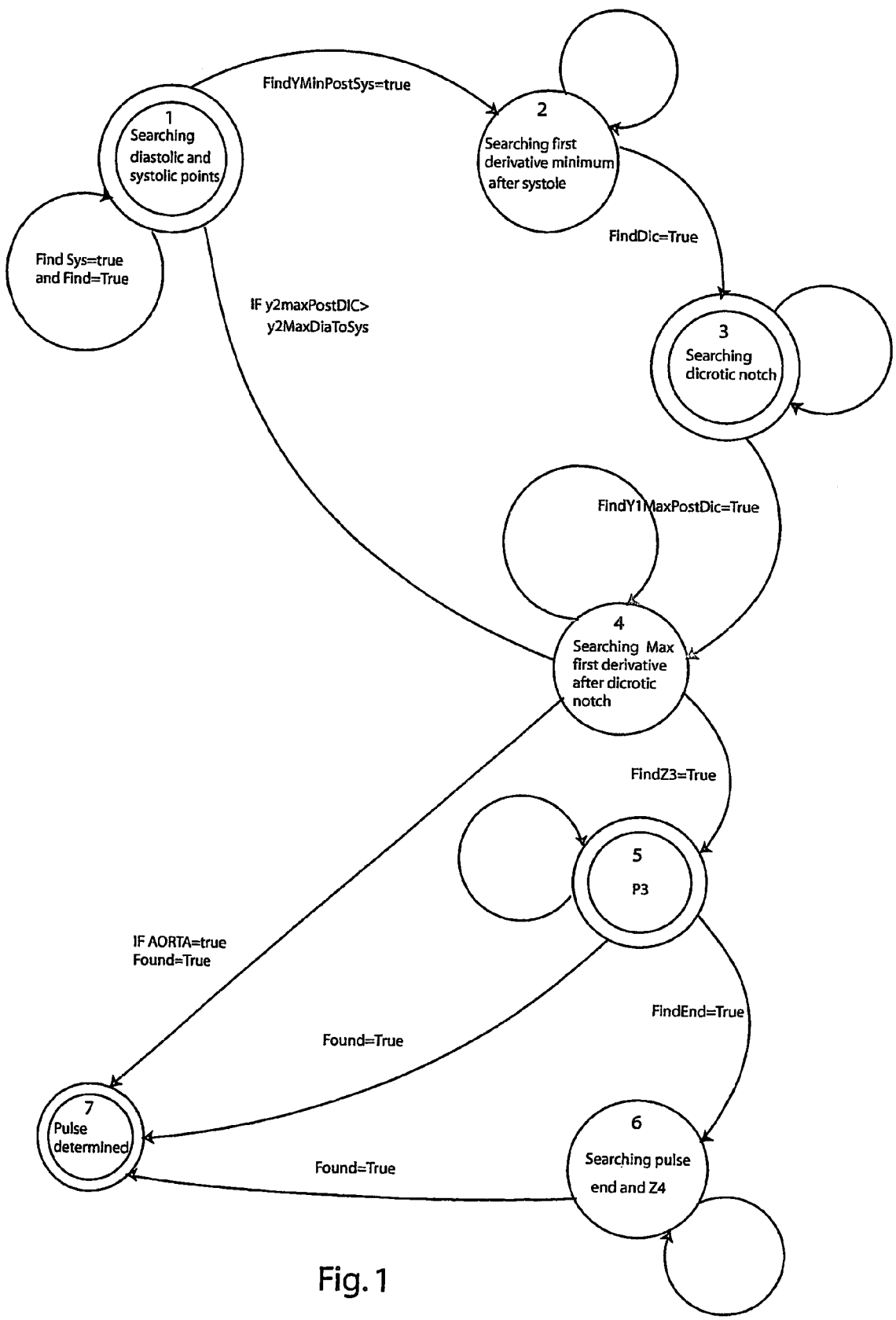
FIG. 1 shows a schematic diagram of the state machine according to which a preferred embodiment of the method according to the invention operates.

With reference to FIG. 1, it may be observed that the state machine, according to which the method according to the invention operates, comprises seven main states.

In the first state 1, the method analyses the sequence of available pressure values forming the detected pressure curve so as to determine:

the pressure (relative) minimum value assumed as diastolic point Pdia;

the pressure (relative) maximum value assumed as systolic point Psys;

the maximum value Y1max_postdia of the pressure first derivative included between the diastolic value and the systolic value; and the maximum value Y2max_diatosys of the pressure second derivative included between the diastolic value and the systolic value.

In particular, the pressure first derivative is proportional to the difference between the values at two consecutive instants of the pressure curve, and the pressure second derivative is proportional to the difference between the values at two consecutive instants of the pressure first derivative. More precisely, the proportionality coefficient is equal to the inverse of the difference between two consecutive instants, i.e. to the inverse of the pressure signal sampling period. Without losing validity, the preferred embodiment of the method assumes as unitary the difference between two consecutive instants, thereby the pressure first derivative is equal to the difference between the values at two consecutive instants of the pressure curve, and the pressure second derivative is equal to the difference between the values at two consecutive instants of the first derivative.

In the following, it has to be considered that the sampled points of the pressure curve, and the related derivatives, are considered one-by-one in time sequence. Preferably, the detected pressure curve is sampled at a frequency of 1 kHz, thereby the pressure values of the sequence are spaced each other by 1 millisecond.

Figure 2:
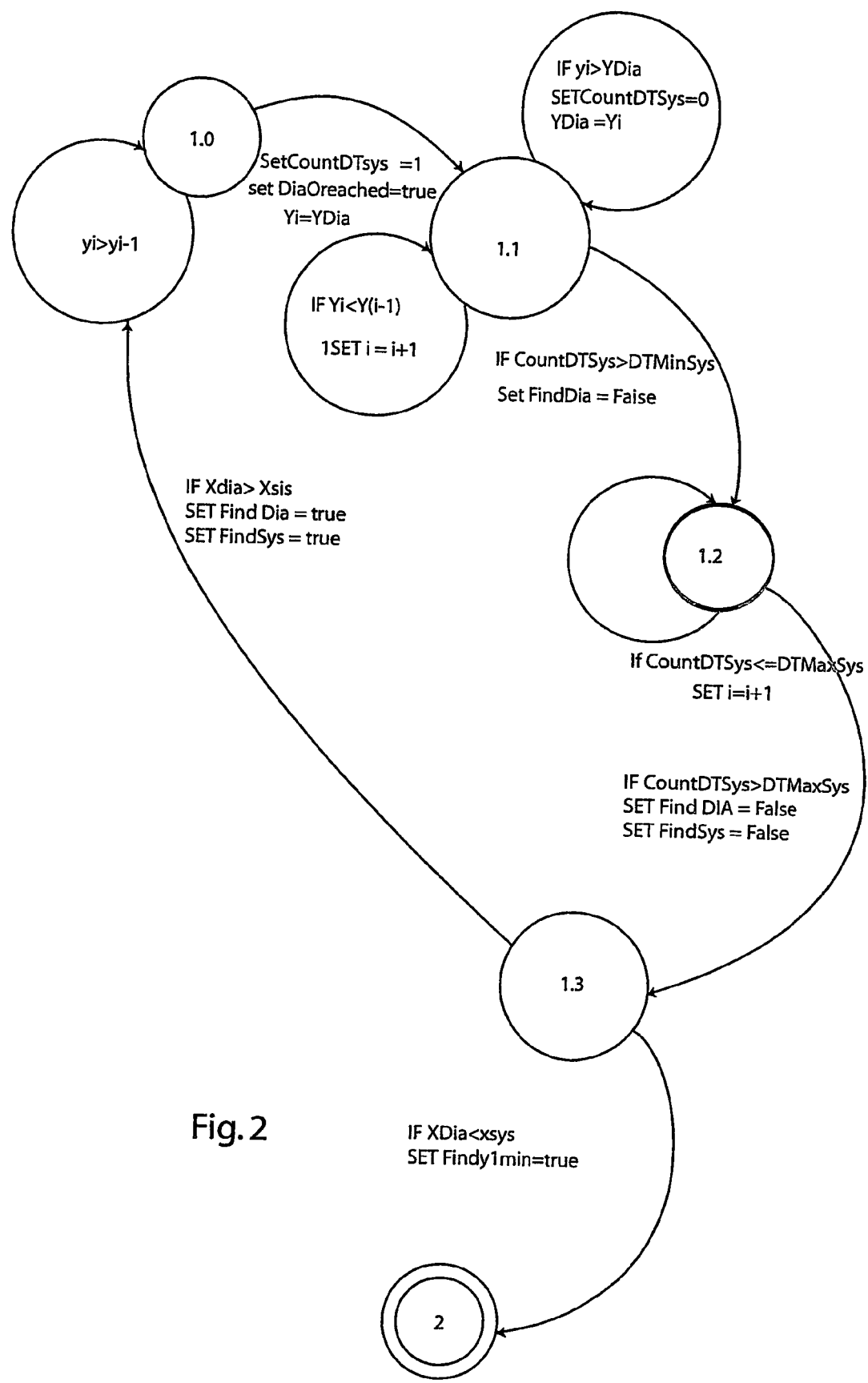
FIG. 2 shows a schematic diagram of the first state of the state machine of FIG. 1.

With reference to FIG. 2, it may be observed that the state 1 comprises 4 sub-states.

In the sub-state 1.0, it is determined the first point Pdec belonging to a decreasing phase of the pressure curve, that hence introduces reaching a relative minimum point. Preferably, such determination is carried out by searching for the pressure curve first point the value of which is less than the value of the preceding point. As soon as such point Pdec is determined, the method passes to the following sub-state 1.1.

In the sub-state 1.1, the method searches for the absolute minimum point Pmin of the pressure curve. In the preferred embodiment of the method according to the invention shown in the Figures, the search for the point Pmin occurs by comparing the value of each curve point P(i) with the value of the point Pmin_current that stores the point having minimum value in the curve section previously examined (comprising the points from Pdec to the point P(i−1) immediately preceding the point P(i) under consideration), so that Pmin_current is updated with the point P(i) with which it is compared, i.e.

$$Pmin\_current = P(i) \quad [1],$$

in the case when the latter has a lower value, i.e. in the case when $$Pmin\_current > P(i) \quad [2];$$

Pmin_current may be preliminarily initialised to the point Pdec determined in the state 1.0.

In the sub-state 1.1, the method also searches for the absolute maximum point Pmax of the pressure curve. In the embodiment shown in the Figures, Pmax is also searched, similarly to Pmin, through the comparison of the value of each curve point P(i) with the value of the point Pmax_current that stores the point having maximum value in the curve section previously examined (comprising the points from Pdec to the point P(i−1) immediately preceding the point P(i) under consideration), so that Pmax_current is updated with the point P(i) with which it is compared, i.e.

$$Pmax\_current = P(i) \quad [3],$$

in the case when the latter has a larger value, i.e. in the case when $$Pmax\_current < P(i) \quad [4];$$

even Pmax_current may be preliminarily initialised to the point Pdec determined in the state 1.0.

Moreover, the method searches for the maximum value Y1max_postdia of the pressure first derivative following the diastolic point. In particular, in the embodiment shown in the Figures, such maximum value Y1 max_postdia is searched through the comparison of the value of each point Y1 (i) of the first derivative curve with the value of a point Y1 max_current that stores the maximum value of the first derivative in the curve section previously examined, comprising the points starting from the instant corresponding to the point Pmin_current to the point Y(i−1) immediately preceding the point Y(i) under consideration, so that Y1max_current is updated with the point Y1(i) with which it is compared, i.e.

$$Y1max\_current = Y1(i) \quad [5],$$

in the case when the latter has a larger value, i.e. in the case when $$Y1max\_current < Y1(i) \quad [6];$$

Y1max_current may be preliminarily initialised to the value of the pressure curve first derivative corresponding to the point Pmin_current.

The method leaves the sub-state 1.1 and passes to the sub-state 1.2 when the value of the point Pmin_current is not updated for a period longer than a minimum threshold DTMIN_SYS, preferably equal to 200 milliseconds, still more preferably equal to 150 milliseconds. To this end, in the sub-state 1.1 the method set a time counter to zero each time that the point Pmin_current is updated and it increments the same each time that it compares the same with a following pressure curve point P(i), verifying whether the time counter value has exceeded the minimum threshold DTMIN_SYS. Before passing to the sub-state 1.2, the method assumes the point Pmin_current as the absolute minimum point Pmin of the pressure curve. In other words, in the sub-state 1.1, the method considers that the last point Pmin_current could be the diastolic point, and consequently it stops the search thereof, when the pressure curve keeps over its value for a minimum period substantially corresponding to the minimum physiological time distance between diastolic point and systolic point.

In the sub-state 1.2, the method continues the searches for the absolute maximum point Pmax of the pressure curve and for the maximum value Y1max_postdia of the pressure first derivative following the diastolic point. Preferably, the searches occur similarly to those of the sub-state 1.1, whereby, in the embodiment of the method shown in the Figures, they are carried out according to formulas [3] and [4], and [5] and [6], respectively. Such searches continue up to a time distance from the point Pmin equal to a maximum threshold DTMAX_SYS, preferably not longer than 380 milliseconds, still more preferably not longer than 360 milliseconds. To this end, in the sub-state 1.2, at each comparison of a pressure curve point with Pmax_current, the method increments the time counter employed in the sub-state 1.1, verifying whether the time counter value has exceeded the maximum threshold DTMAX_SYS. Before passing to the following sub-state 1.3, the method assumes the point Pmax_current as the absolute maximum point Pmax of the pressure curve, and the value Y1max_current as the maximum value Y1 max_postdia of the pressure first derivative following the diastolic point. In other words, in the sub-state 1.2, the method searches for the systolic point (and the pressure first derivative maximum value following the diastolic point) in a pressure curve interval substantially corresponding to the maximum physiological time distance between diastolic point and systolic point.

The method performs the contemporaneous search for the diastolic point and the systolic point in the sub-state 1.1 for taking into account both the cardiac arrhythmias and counterpulsations (whereby the diastolic and systolic points may be relative, instead of absolute, maximum and minimum points of the pressure curve), and the possible noise introduced into the pressure curve by events not due to the curve physiology, as for instance electric noise, a patient's cough, or the movement of a blood pressure detecting instrument (e.g. a catheter). Such contemporaneous search, in case of high noise, may give the physiologically incorrect result that the absolute minimum point Pmin follows the absolute maximum point Pmax. Therefore, in the sub-state 1.3, the method verifies that the point Pmin determined in the sub-state 1.1 precedes the point Pmax determined in the sub-state 1.1 or 1.2.

If the outcome of the verification is negative, the method returns to perform the sub-state 1.0 starting from the pressure curve point Pmin previously determined. In such a way, the sub-state 1.1 will search for the absolute minimum point following the one previously determined.

If otherwise the verification has given a positive outcome, the absolute minimum point Pmin is assumed as diastolic point Pdia and the absolute maximum point Pmax is assumed as systolic point Psys; also, the method determines the maximum value Y2max_diatosys of the pressure second derivative which is included between the diastolic point and the systolic point. Such determination could furthermore be carried out simultaneously with the searches for the diastolic and systolic points, by suitably modifying the sub-states 1.1 and 1.2. Finally, the method passes to the following second state 2.

The time checks carried out in the sub-states 1.1 and 1.2 allow the method according to the invention to take into account the fact that, when the cardiac frequency varies, the systolic phase is physiologically constant in duration (whereby the systolic point occurs in an interval ranging from about 150 to about 360 milliseconds after the diastolic point), whereas on the contrary the diastolic phase modifies its duration when the frequency varies; hence, the method correctly recognises the diastolic and systolic points even in the case of very low cardiac frequency.

Still making reference to FIG. 1, once the diastolic Pdia and systolic Psys points, and the values Y1max_postdia and Y2max_diatosys are determined, the state machine enters the second state 2, wherein the method according to the invention searches for the absolute minimum value Y1 min_postsys of the pressure first derivative after systole in an interval of duration equal to DTMAX_MINY1_SYS following the systole; in particular, DTMAX_MINY1_SYS is equal to the maximum duration of the physiological interval wherein the pressure first derivative minimum value follows the systolic point, and it is preferably not longer than 250 milliseconds, still more preferably not longer than 200 milliseconds. In such a way, the method determines the inflection point Pinflection following the pressure curve systole wherein the pressure first derivative assumes the absolute minimum value Y1 min_postsys, in order to discriminate the cases when the pressure curve is detected under high noise conditions, whereby the pressure signal shape may present a small hump, or a short plateau, immediately following the systole and in which the method could then wrongly recognise a dicrotic point. Instead, the determination of the absolute minimum value Y1min_postsys correctly shifts the search for the dicrotic notch beyond these small humps, or plateaus, immediately following the systole.

Afterwards, the state machine enters the third state 3, wherein the method according to the invention searches for the dicrotic point.

Figure 3:
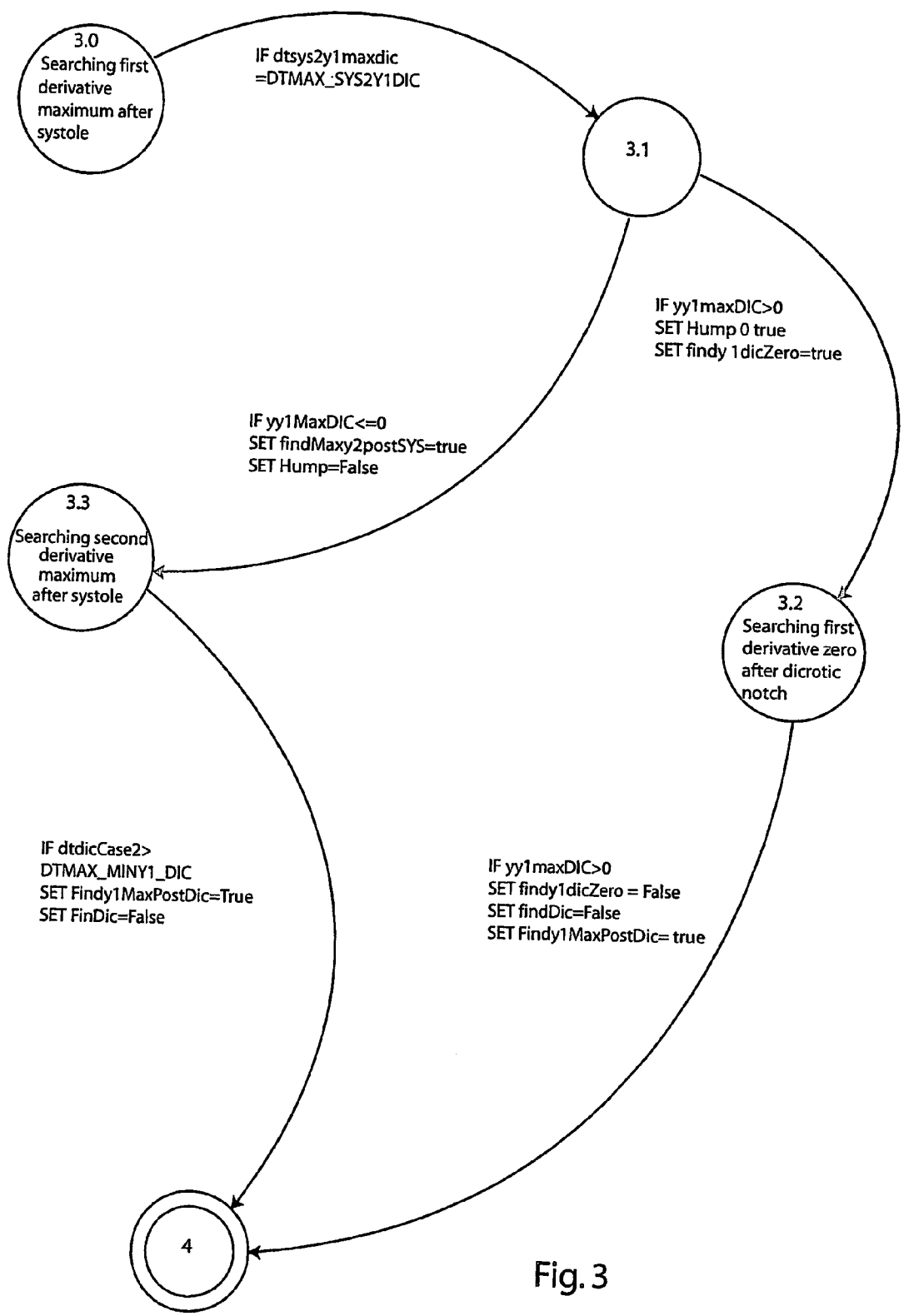
FIG. 3 shows a schematic diagram of the third state of the state machine of FIG. 1.

With reference to FIG. 3, it may be observed that the state 3 comprises 4 sub-states.

In the sub-state 3.0, in a time interval of duration equal to DTMAX_SYS2Y1DIC following the inflection point Pinflection, the first derivative absolute maximum point Y1max_postsys is determined, then passing to the following sub-state 3.1. In particular, DTMAX_SYS2Y1DIC is equal to the maximum duration of the physiological interval wherein the dicrotic notch follows the inflection point, and it is preferably not longer than 250 milliseconds, still more preferably not longer than 200 milliseconds.

In the sub-state 3.1, the method verifies whether the point Y1max_postsys determined in the sub-state 3.0 is positive.

Figure 4:
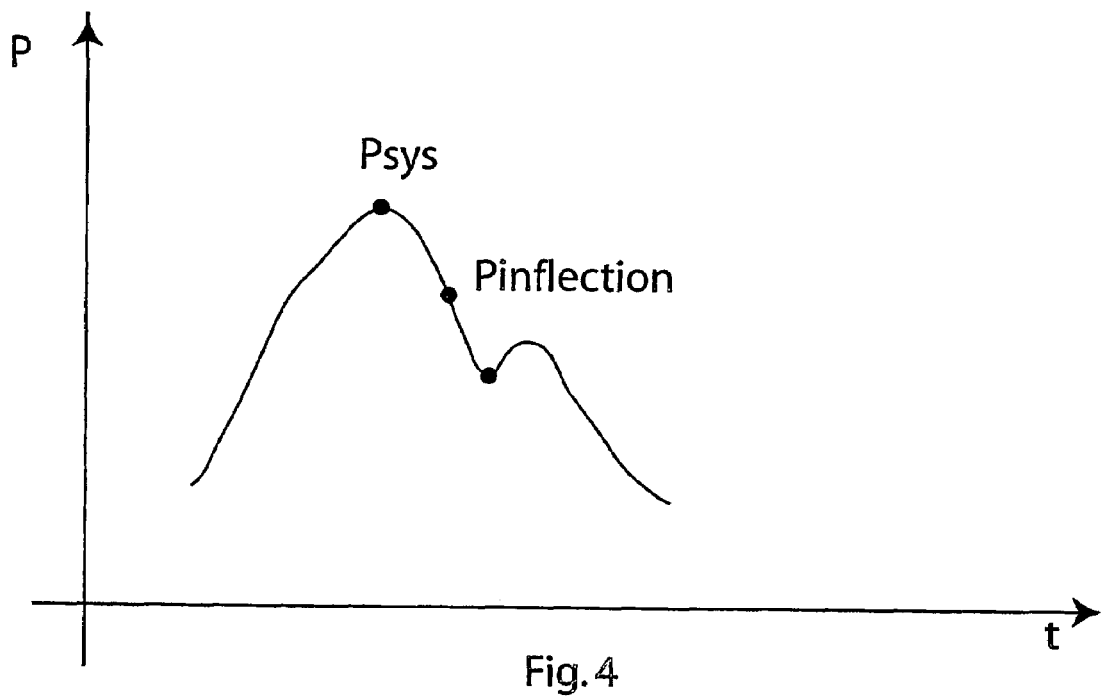
FIG. 4 shows a first pressure curve detected and analysed through the preferred embodiment of the method according to the invention.
Figure 5:
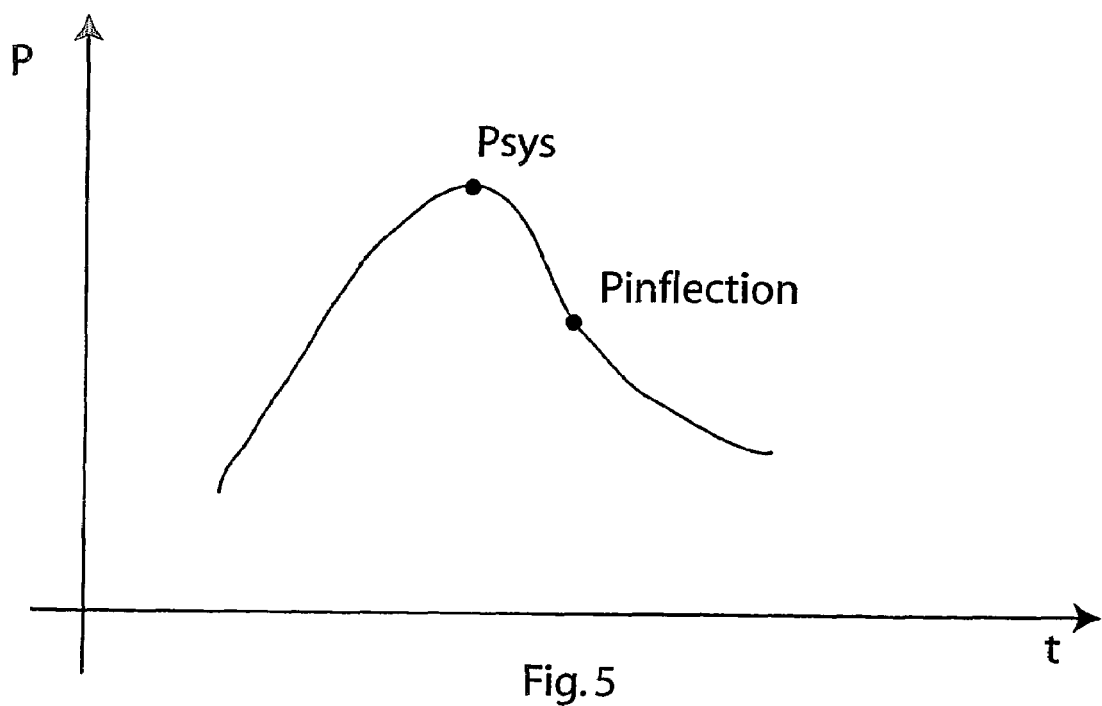
FIG. 5 shows a second pressure curve detected and analysed through the preferred embodiment of the method according to the invention.

If the outcome of the verification is positive, it means that the pressure curve presents a hump after the dicrotic point, as schematically shown in FIG. 4, whereby in this case the dicrotic point Pdic corresponds to the pressure curve first relative minimum point following the inflection point Pinflection determined in the second state 2. Therefore, the method performs the sub-state 3.2 wherein it determines such point Pdic, by determining the instant wherein the pressure curve first derivative assumes the value of zero in the time interval of duration equal to DTMAX_SYS2Y1DIC following the inflection point Pinflection. The method then passes to the next fourth state 4.

Instead, in the case when the outcome of the sub-state 3.1 verification has been negative, or the first derivative absolute maximum point Y1max_postsys determined in the sub-state 3.0 is non-positive, the pressure curve does not present any hump after the dicrotic point, and the latter correspond to the point wherein the pressure second derivative assumes the maximum value. Therefore, the method performs the sub-state 3.3 wherein it determines the dicrotic point Pdic, by determining the instant wherein the pressure curve second derivative assumes the maximum value Y2max_postinflection in the time interval of duration equal to DTMAX_SYS2Y1DIC following the inflection point Pinflection. The method then passes to the next fourth state 4.

Still making reference to FIG. 1, the state machine enters the fourth state 4, wherein the method according to the invention determines the first derivative maximum value Y1max_postdic and the pressure curve second derivative maximum value Y2max_postdic after the dicrotic point Pdic determined in the third state 3. Such search is carried out in the interval DPOSTDIC following the dicrotic point, preferably not longer than 150 milliseconds. Afterwards, the method verifies whether at least one of the two maximum values Y1 max_postdia and Y2max_diatosys, belonging to, respectively, the first derivative and the pressure second derivative, following the diastolic point, which are determined in the first state 1, is less than the just determined value of the corresponding derivative, respectively Y1 max_postdic and Y2max_postdic. Such verification is necessary in order to discriminate the case wherein, when particular pressure signals having a hump after the dicrotic notch are present, the determined dicrotic point Pdic is actually a diastolic point. This is the example of the pressure curve detected for a heart particularly elastic (such as the one of an athlete) under stress, wherein it is possible to verify that the dicrotic point has a pressure value less than the one of the diastolic point. However, even in this case the physiological increase rate of the pressure curve along the section between diastolic point and systolic point is larger than the physiological increase rate of the pressure curve after the dicrotic point. This is discriminated by just comparing the maximum values of first and second derivatives after, respectively, the point assumed as diastolic point and the point assumed as dicrotic point.

In this regard, other embodiments of the method according to the innovation perform in the fourth state 4 the determination of the values Y1max_postdic and Y2max_postdic, and their comparison with the values Y1 max_postdia and Y2max_diatosys, only in the case when in the third state 3 the presence of a hump after the dicrotic point has been ascertained.

In the case when the verification gives a positive outcome, (i.e. at least one of the two values Y1max_postdia and Y2max_diatosys is less than, respectively, Y1max_postdic or Y2max_postdic) the determined diastolic Pdia point, systolic Psys point, and dicrotic Pdic point do not correspond to a physiologically correct pressure curve and the method returns to perform the sub-state 1.0 of the first state 1, starting from a point following Pdia, that has been determined as diastolic point and preceding Pdic determined as dicrotic point, for determining diastolic and/or systolic and/or dicrotic points different from those previously determined. Preferably, the method returns to perform the sub-state 1.0 of the first state 1, starting from the point immediately preceding the point Pdic determined in the third state 3 as dicrotic point.

In the case when the verification gives a negative outcome, (i.e. both the values Y1max_postdia and Y2max_diatosys are larger than, respectively, the values Y1max_postdic and Y2max_postdic), the determined points Pdia, Psys, and Pdic are physiologically correct and the method further verifies whether the pressure curve has been detected in aorta.

In the positive, the method directly passes to a final state 7, wherein it gives all the detected data as characteristic data of the beat of which it has examined the pressure curve and it possibly returns to perform the first state 1 for examining the following beat.

In the negative (the pressure curve has been detected in aorta), the method passes to a fifth state 5, wherein it determines the pressure curve point P3 corresponding to the instant t3 wherein the curve second derivative assumes the minimum value Y2 min_systodic along the interval between the systolic point and the dicrotic point. Preferably, the interval goes from the point being intermediate of the interval included between the systolic point Psys and the dicrotic point Pdic, to the following point Pdic. In other words, the interval wherein the value Y2 min_systodic is determined preferably goes from the instant:

$$tsys+(tdic-tsys)/2$$

up to the instant $$tdic,$$

where tsys is the instant corresponding to the systolic point and tdic is the instant corresponding to the dicrotic point.

Afterwards, in the case when in the third state 3 the presence of a hump along the pressure curve has not been recognised, the method passes to perform the final state 7; otherwise (in the third state 3 it has been ascertained that the pressure curve presents a hump), the method passes to perform a sixth state 6.

In the sixth state 6, the method searches for the relative maximum point P4 after the dicrotic point, i.e. the hump apex, corresponding to the instant wherein the pressure curve first derivative assumes the non-negative minimum value within the interval following the dicrotic point. In particular, the search for the point P4 is carried out Within the interval DPOSTDIC following the dicrotic notch.

Moreover, in the sixth state 6, the method also searches for the relative minimum point Pend after the dicrotic point, i.e. the end of the beat under examination. In particular, the search for the point Pend is carried out along the interval going from the point P4 up to the point Ptermination distant by DENDPOSTDIC from the dicrotic point Pdic, equal to the maximum physiological time distance between the dicrotic point and a following anomalous beat (extrasystole) or accelerated beat (high cardiac frequencies); preferably, DENDPOSTDIC is not longer than 150 milliseconds. Finally, the method passes to perform the final state 7.

As said, in the final state 7, the method gives all the detected data as characteristic data of the beat of which it has examined the pressure curve and possibly returns to perform the first state 1 for examining the following beat. In particular, in the case when the state 7 is reached from the state 4 or the state 5, the method returns to perform the first state 1 starting from a point following the dicrotic point Pdic by an interval DNEW, preferably not shorter than 1 millisecond and not longer than 150 milliseconds; in the case when the state 7 is reached from the state 6, the method returns to perform the sub-state 1.0 of the first state 1 starting from a point following the dicrotic point Pdic and preceding the determined point Pend (preferably starting from the point immediately preceding the determined point Pend), or, in the case when the point Pend has not been determined, from a point following the dicrotic point Pdic and not following the point Ptermination (preferably starting from the point immediately preceding the determined point Ptermination).

The advantages obtained through the method according to the invention are numerous.

First of all, the method is capable to obtain the pulse recognition from the analysis of the pressure curve produced by the heart during its operation, reliably delimiting the start and end points of each beat.

Moreover, the method is capable to discriminate the cases wherein the diastolic and systolic points are relative, and not absolute, minimum and maximum points, when the pressure curve also presents other minimum and maximum points. In fact, the diastolic and systolic points are recognised as valid only if when passing from one to the other the first derivative (and also the second derivative) of the pressure curve reaches its maximum within the whole beat.

Still, the method determines the diastolic, systolic, and dicrotic points by examining time intervals rather long around the maximum or minimum or inflection points.

The program determines the diastolic, systolic, and dicrotic points within time limits physiologically depending on the site where the pressure is detected. In particular, the actual closure of the pulse occurs after that the diastolic, systolic, and dicrotic points of the following beat have been determined.

The method according to the invention also permits, in case of very low frequency, to determine the beat notwithstanding the limits imposed upon the time between dicrotic notch and diastole, because it takes into account the fact that the systolic phase is physiologically of duration not very variable when the cardiac frequency varies, whereas on the contrary the diastolic phase modifies its duration when the frequency varies.

Furthermore, the method according to the invention allows the signal of an electrocardiogram to be reliably studied.

The preferred embodiments have been above described and some modifications of this invention have been suggested, but it should be understood that those skilled in the art can make other variations and changes, without so departing from the related scope of protection, as defined by the following claims.

The invention claimed is:

1. Automated method for discriminating the cardiac beat, on the basis of a blood pressure sampled signal, having a starting point Pstart, characterised in that it operates according to a finite state machine, comprising:
    a first state (1), wherein the method searches for:
        a pressure absolute minimum value Pmin, by scanning pressure values included within a first time interval not exceeding the interval going from the starting point Pstart up to the point distant from the determined minimum value Pmin by a first time threshold DTMIN_SYS,
        a pressure absolute maximum value Pmax, by scanning the pressure values included within a second time interval not exceeding the interval going from the starting point Pstart up to the point distant from the determined minimum value Pmin by a second time threshold DTMAX_SYS, and
        a pressure signal first derivative maximum value Y1max_postdia included within a third time threshold not exceeding the interval going from the starting point Pstart up to the point distant from the determined minimum value Pmin by a period equal to the second time threshold DTMAX_SYS,
    the method assuming the point Pmin as diastolic point Pdia and the point Pmax as systolic point Psys, and passing to a following second state (2);
    the second state (2), wherein the method searches for a pressure signal inflection point Pinflection following the systolic point Psys in a fifth time interval not exceeding the interval starting from the systolic point Psys and of duration equal to a third time threshold DTMAX_MINY1_SYS, the method then passing to a following third state (3);
    the third state (3), wherein the method verifies whether, in a sixth time interval not exceeding the interval starting from the inflection point Pinflection and of duration equal to a fourth time threshold DTMAX_SYS2Y1DIC, the pressure signal presents a hump with downward concavity, so that:
        if the outcome of the verification is positive, the method searches, in a seventh time interval not exceeding the interval starting from the inflection point Pinflection and of duration equal to the fourth time threshold DTMAX_SYS2Y1DIC, for the first pressure curve relative minimum, and it assumes the latter as dicrotic point Pdic, whereas
        if the outcome of the verification is negative, the method searches in said seventh time interval the instant wherein the pressure signal second derivative assumes the maximum value Y2max_postinflection, and it assumes the related pressure signal point as dicrotic point Pdic,
    the method then passing to a following fourth state (4);
    the fourth state (4), wherein the method searches for a maximum value Y1max_postdic of the pressure signal first derivative in an eighth interval not exceeding the interval starting from the dicrotic point Pdic and of duration equal to a fifth time threshold DPOSTDIC, the method verifying that the maximum value Y1max_postdia determined in the first state (1) is not less than the value Y1max_postdic, so that:
        if the outcome of the verification is negative, the method returns to the first state (1) assuming as new starting point Pstart a point following the diastolic point Pdia and not following the dicrotic point Pdic, whereas
        if the outcome of the verification is positive, the method passes to a final state (7); and
    the final state (7), wherein the method is apt to give the diastolic point Pdia, the systolic point Psys, and the dicrotic point Pdic.

2. Method according to claim 1, characterised in that in the first state(1) it also searches for:
    a pressure signal second derivative maximum value Y2max_diatosys included within a fourth time interval not exceeding the interval going from the starting point Pstart up to the point distant from the determined minimum value Pmin by a period equal to the second time threshold DTMAX_SYS,
    and in that in the fourth state (4) it also searches for a pressure signal second derivative maximum value Y2max_postdic within the eighth interval, the method also verifying that the maximum value Y2max_diatosys determined in the first state (1) is not less than the value Y2max_postdic, so that:
        if the outcome of the verification is negative, the method returns to the first state (1) assuming as new starting point Pstart a point following the diastolic point Pdia and not following the dicrotic point Pdic, whereas
        if the outcome of the verification is positive, the method passes to the final state (7).

3. Method according to claim 1, characterised in that in the first state (1), the assumption of the points Pmin and Pmax as diastolic Pdia and systolic Psys points, respectively, depends on the outcome of the verification that the point Pmin precedes the point Pmax, so that:
    if the outcome of the verification is negative, the method returns to perform all the operations of the first state (1) assuming as new starting point Pstart a point not preceding Pmin, whereas
    if the outcome of the verification is positive, the point Pmin is assumed as diastolic point Pdia and the point Pmax is assumed as systolic point Psys and the method passes to the following second state (2).

4. Method according to claim 1, characterised in that the finite state machine according to which it operates comprises a fifth state (5), the method passing from the fourth state (4) to the final state (7) by preliminarily passing to the fifth state (5), wherein the method determines a pressure signal point P3 corresponding to the instant t3 wherein the pressure signal second derivative assumes the absolute minimum value Y2min_systodic within a ninth interval not exceeding the interval going from the systolic point Psys up to the dicrotic point Pdic, the method then passing to the final state (7) wherein it is apt to give the point P3.

5. Method according to claim 4, characterised in that said ninth interval goes from the instant which is intermediate within the interval included between the systolic point Psys and the dicrotic point Pdic tsys+(tdic−tsys)/2 up to the instant of the dicrotic point Pdic tdic, where tsys is the instant corresponding to the systolic point Psys and tdic is the instant corresponding to the dicrotic point Pdic.

6. Method according to claim 4, characterised in that in the fourth state (4) the method verifies whether the pressure signal has been detected in an aorta, so that:
   if the outcome of the verification is positive, the method passes to the final state (7), whereas
   if the outcome of the verification is negative, the method passes to the fifth state (5).

7. Method according to claim 1, characterised in that the finite state machine according to which it operates comprises a sixth state (6), at which the method arrives in the case when in the third state (3) it has verified that the pressure signal presents a hump with downward concavity within the sixth time interval, the method arriving at the sixth state (6) after the fourth state (4) before passing to the final state (7), in the sixth state (6) the method searching in said sixth time interval for the relative maximum point P4 after the dicrotic point Pdic, i.e. the hump apex, the method then passing to the final state (7) wherein it is apt to give the point P4.

8. Method according to claim 7, characterised in that in the sixth state (6) the method also searches for a pressure signal relative minimum point Pend within a tenth interval not exceeding the interval going from the dicrotic point Pdic up to the point Ptermination distant from the dicrotic point Pdic by a sixth time threshold DENDPOSTDIC, the method being apt to give in the final state (7) the point Pend in the case when this has been determined in the sixth state (6).

9. Method according to claim 8, characterised in that the method searches for the point Pend after having determined the point P4 and in that said tenth interval goes from the point P4 up to the point Ptermination.

10. Method according to claim 8, characterised in that the sixth time threshold DENDPOSTDIC is not longer than 150 milliseconds.

11. Method according to claim 7, when characterised in that the method arrives at the sixth state (6) starting from the fifth state (5).

12. Method according to claim 1, characterised in that in the first state (1) it searches for the first point Pdec following the starting point Pstart belonging to a pressure signal decreasing phase, in that the first time interval goes from the first decreasing point Pdec up to the point distant from the determined minimum value Pmin by a first time threshold DTMIN_SYS, and in that the second time interval goes from the first decreasing point Pdec up to the point distant from the determined minimum value Pmin by a second time threshold DTMAX_SYS.

13. Method according to claim 12, characterised in that the third and the four time intervals go from the first decreasing point Pdec up to the point distant from the determined minimum value Pmin by a second time threshold DTMAX_SYS.

14. Method according to claim 1, characterised in that the third and the four time intervals go from the determined minimum value Pmin up to the point distant from the determined minimum value Pmin by a second time threshold DTMAX_SYS.

15. Method according to claim 1, characterised in that the third and the four time intervals go from the determined minimum value Pmin up to the determined maximum value Pmax.

16. Method according to claim 1, characterised in that in the second state (2) it searches for the point Pinflection by searching for the pressure signal first derivative absolute minimum value Y1min_postsys within the fifth time interval, assuming the pressure signal point wherein the first derivative thereof assumes the absolute minimum value Y1min_postsys as inflection point Pinflection.

17. Method according to claim 1, characterised in that in the third state (3) it verifies whether in the sixth time interval the pressure signal presents a hump with downward concavity by searching for the pressure signal first derivative absolute maximum value Y1max_postsys and by verifying that this value Y1max_postsys is positive, whereby the pressure signal presents said hump in the case when the value Y1max_postsys is positive.

18. Method according to claim 1, characterised in that in the third state (3) it searches within the seventh time interval for the pressure curve first relative minimum by searching for the instant wherein the pressure signal first derivative assumes the value of zero within said seventh time interval.

19. Method according to claim 1, characterised in that, in the fourth state (4), the search for the first derivative maximum value Y1max_postdic and the second derivative maximum value Y2max_postdic of the pressure signal within the eighth interval, and the verification that both are not larger than the maximum values Y1max_postdia and Y2max_diatosys determined in the first state (1), are carried out only in the case when in the third state (3) the method has verified that the pressure signal presents a hump with downward concavity within the sixth time interval.

20. Method according to claim 1, characterised in that, when it returns from the fourth state (4) to the first state (1), the method assumes the point immediately preceding the determined dicrotic point Pdic as new starting point Pstart.

21. Method according to claim 1, characterised in that the first time threshold DTMIN_SYS is not longer than 200 milliseconds.

22. Method according to claim 21, characterised in that the first time threshold DTMIN_SYS is not longer than 150 milliseconds.

23. Method according to claim 1, characterised in that the second time threshold DTMAX_SYS is not longer than 380 milliseconds.

24. Method according to claim 23, characterised in that the second time threshold DTMAX_SYS is not longer than 350 milliseconds.

25. Method according to claim 1, characterised in that the third time threshold DTMAX_MINY1_SYS is not longer than 250 milliseconds.

26. Method according to claim 25, characterised in that the third time threshold DTMAX_MINY1_SYS is not longer than 200 milliseconds.

27. Method according to claim 1, characterised in that the fourth time threshold DTMAX_SYS2Y1DIC is not longer than 250 milliseconds.

28. Method according to claim 27, characterised in that the fourth time threshold DTMAX_SYS2Y1DIC is not longer than 200 milliseconds.

29. Method according to claim 1, characterised in that the fifth time threshold DPOSTDIC is not longer than 200 milliseconds.

30. Method according to claim 29, characterised in that the fifth time threshold DPOSTDIC is not longer than 150 milliseconds.

31. Method according to claim 1, characterised in that the pressure signal is sampled at a frequency of 1 kHz.

32. Method according to claim 8, characterised in that from the final state (7) it returns to iteratively perform the first state (1) by assuming a point following the dicrotic point Pdic as new starting point Pstart.

33. Method according to claim 32, characterised in that from the final state (7) it returns to iteratively perform the first state (1) by assuming a point following the dicrotic point Pdic and distant from this by a seventh time threshold DNEW as new starting point Pstart.

34. Method according to claim 33, characterised in that the seventh time threshold DNEW is not shorter than 1 millisecond and not longer than 150 milliseconds.

35. Method according to claim 32, characterised in that, in the case when in the sixth state (6) the point Pend has been determined, from the final state (7) the method returns to iteratively perform the first state (1) by assuming a point following the dicrotic point Pdic and preceding the point Pend as new starting point Pstart.

36. Method according to claim 35, characterised in that, in the case when in the sixth state (6) the point Pend has been determined, from the final state (7) the method returns to iteratively perform the first state (1) by assuming the point immediately preceding the point Pend as new starting point Pstart.

37. Method according to claim 32, characterised in that, in the case when in the sixth state (6) the point Pend has not been determined, from the final state (7) the method returns to iteratively perform the first state (1) by assuming a point following the dicrotic point Pdic and not following the point Ptermination as new starting point Pstart.

38. Method according to claim 37, characterised in that, in the case when in the sixth state (6) the point Pend has not been determined, from the final state (7) the method returns to iteratively perform the first state (1) by assuming the point immediately preceding the point Ptermination as new starting point Pstart.

39. Method according to claim 1, characterised in that from the final state (7) it returns to iteratively perform the first state (1) by assuming a point following the dicrotic point Pdic as new starting point Pstart.

40. Computer, comprising:
input and/or output interface means,
memorising means,
processing means, and
program code executable by the processing computer to control the computer to function for discriminating the cardiac beat, on the basis of a blood pressure sampled signal, having a starting point Pstart, operating according to a finite state machine, with
a first state (1), wherein the method searches for:
a pressure absolute minimum value Pmin, by scanning pressure values included within a first time interval not exceeding the interval going from the starting point Pstart up to the point distant from the determined minimum value Pmin by a first time threshold DTMIN SYS,
a pressure absolute maximum value Pmax, by scanning the pressure values included within a second time interval not exceeding the interval going from the starting point Pstart up to the point distant from the determined minimum value Pmin by a second time threshold DTMAX SYS, and a pressure signal first derivative maximum value Y1max postdia included within a third time threshold not exceeding the interval going from the starting point Pstart up to the point distant from the determined minimum value Pmin by a period equal to the second time threshold DTMAX SYS, the method assuming the point Pmin as diastolic point Pdia and the point Pmax as systolic point Psys, and passing to a following second state (2);

the second state (2), wherein the method searches for a pressure signal inflection point Pinflection following the systolic point Psys in a fifth time interval not exceeding the interval starting from the systolic point Psys and of duration equal to a third time threshold DTMAX MINY1SYS, the method then passing to a following third state (3);

the third state (3), wherein the method verifies whether, in a sixth time interval not exceeding the interval starting from the inflection point Pinflection and of duration equal to a fourth time threshold DTMAX SYS2Y1DIC, the pressure signal presents a hump with downward concavity, so that:

if the outcome of the verification is positive, the method searches, in a seventh time interval not exceeding the interval starting from the inflection point Pinflection and of duration equal to the fourth time threshold DTMAX SYS2Y1DIC, for the first pressure curve relative minimum, and it assumes the latter as dicrotic point Pdic, whereas if the outcome of the verification is negative, the method searches in said seventh time interval the instant wherein the pressure signal second derivative assumes the maximum value Y2max postinflection, and it assumes the related pressure signal point as dicrotic point Pdic, the method then passing to a following fourth state (4);

the fourth state (4), wherein the method searches for a maximum value Y1max postdic of the pressure signal first derivative in an eighth interval not exceeding the interval starting from the dicrotic point Pdic and of duration equal to a fifth time threshold DPOSTDIC, the method verifying that the maximum value Y1max postdia determined in the first state (1) is not less than the value Y1max postdic, so that:

if the outcome of the verification is negative, the method returns to the first state (1) assuming as new starting point Pstart a point following the diastolic point Pdia and not following the dicrotic point Pdic, whereas if the outcome of the verification is positive, the method passes to a final state (7); and the final state (7), wherein the method is apt to give the diastolic point Pdia, the systolic point Psys, and the dicrotic point Pdic.

41. The computer of claim 40 in combination with a blood pressure detecting means.

42. A computer readable storage medium storing instructions executable by a computer to control the computer to function for discriminating the cardiac beat, on the basis of a blood pressure sampled signal, having a starting point Pstart, characterised in that it operates according to a finite state machine, comprising:

a first state (1), wherein the method searches for:
a pressure absolute minimum value Pmin, by scanning pressure values included within a first time interval not exceeding the interval going from the starting point Pstart up to the point distant from the determined minimum value Pmin by a first time threshold DTMIN SYS, a pressure absolute maximum value Pmax, by scanning the pressure values included within a second time interval not exceeding the interval going from the starting point Pstart up to the point distant from the determined minimum value Pmin by a second time threshold DTMAX SYS, and a pressure signal first derivative maximum value Y1max postdia included within a third time threshold not exceeding the interval going from the starting point Pstart up to the point distant from the determined minimum value Pmin by a period equal to the second time threshold DTMAX SYS, the method assuming the point Pmin as diastolic point Pdia and the point Pmax as systolic point Psys, and passing to a following second state (2);

the second state (2), wherein the method searches for a pressure signal inflection point Pinflection following the systolic point Psys in a fifth time interval not exceeding the interval starting from the systolic point Psys and of duration equal to a third time threshold DTMAX MINY1SYS, the method then passing to a following third state (3);

the third state (3), wherein the method verifies whether, in a sixth time interval not exceeding the interval starting from the inflection point Pinflection and of duration equal to a fourth time threshold DTMAX SYS2Y1DIC, the pressure signal presents a hump with downward concavity, so that:

if the outcome of the verification is positive, the method searches, in a seventh time interval not exceeding the interval starting from the inflection point Pinflection and of duration equal to the fourth time threshold DTMAX SYS2Y1DIC, for the first pressure curve relative minimum, and it assumes the latter as dicrotic point Pdic, whereas if the outcome of the verification is negative, the method searches in said seventh time interval the instant wherein the pressure signal second derivative assumes the maximum value Y2max postinflection, and it assumes the related pressure signal point as dicrotic point Pdic, the method then passing to a following fourth state (4);

the fourth state (4), wherein the method searches for a maximum value Y1max postdic of the pressure signal first derivative in an eighth interval not exceeding the interval starting from the dicrotic point Pdic and of duration equal to a fifth time threshold DPOSTDIC, the method verifying that the maximum value Y1max postdia determined in the first state (1) is not less than the value Y1max postdic, so that:

if the outcome of the verification is negative, the method returns to the first state (1) assuming as new starting point Pstart a point following the diastolic point Pdia and not following the dicrotic point Pdic, whereas if the outcome of the verification is positive, the method passes to a final state (7); and the final state (7), wherein the method is apt to give the diastolic point Pdia, the systolic point Psys, and the dicrotic point Pdic.

* * * * *